(12) United States Patent
Dubois et al.

(10) Patent No.: US 9,228,212 B2
(45) Date of Patent: Jan. 5, 2016

(54) METHOD FOR PRODUCING RICINOLEIC ACID ESTER BY SELECTIVE ENZYMATIC TRANSESTERIFICATION

(75) Inventors: Jean-Luc Dubois, Millery (FR); Claire Bourlieu-Lacanal, Rennes (FR); Jerome Lecomte, St Gely du Fesc (FR); Eric Dubreucq, Montpellier (FR); Pierre Villeneuve, Montpellier (FR)

(73) Assignee: ARKEMA FRANCE, Colombes (FR)

( * ) Notice: Subject to any disclaimer, the term of this patent is extended or adjusted under 35 U.S.C. 154(b) by 613 days.

(21) Appl. No.: 13/254,089

(22) PCT Filed: Feb. 24, 2010

(86) PCT No.: PCT/FR2010/050314
§ 371 (c)(1),
(2), (4) Date: Nov. 14, 2011

(87) PCT Pub. No.: WO2010/100366
PCT Pub. Date: Sep. 10, 2010

(65) Prior Publication Data
US 2012/0065419 A1 Mar. 15, 2012

(30) Foreign Application Priority Data
Mar. 2, 2009 (FR) .................................. 09 51302

(51) Int. Cl.
*C12P 7/64* (2006.01)
*C11C 1/08* (2006.01)
(Continued)

(52) U.S. Cl.
CPC ................ *C12P 7/6454* (2013.01); *C11C 1/08* (2013.01); *C11C 3/003* (2013.01); *C12P 7/649* (2013.01); *C12P 7/6436* (2013.01); *C12P 13/005* (2013.01); *Y02E 50/13* (2013.01)

(58) Field of Classification Search
None
See application file for complete search history.

(56) References Cited

U.S. PATENT DOCUMENTS 4,275,011 A * 6/1981 Tanaka et al. ................. 435/134
5,470,741 A * 11/1995 Oester et al. ............... 435/254.1
(Continued)

FOREIGN PATENT DOCUMENTS

WO WO93/02180 2/1993

OTHER PUBLICATIONS

Watanabe, et al., Continuous produciton fo biodiesel fuel form vegetable oil using immobolized *Candida antarctica* Lipase, 2000, JAOCS, vol. 77, No. 4, pp. 355-360.*
(Continued)

*Primary Examiner* — Yate K Cutliff
(74) *Attorney, Agent, or Firm* — Smith, Gambrell & Russell, LLP (57) ABSTRACT

The present invention relates to a method for preparing ricinoleic acid ester from a pure or mixed vegetable oil, in particular castor oil, wherein the method includes at least the step of enzymatic transesterification in the presence of a light alcohol and using a typo-selective lipase in order to obtain a fraction enriched with ricinoleic acid ester. The method according to the invention for producing ricinoleic acid ester includes the steps: i) a first transesterification reaction in the presence of a light alcohol and a lipase extracted from *Geotrichum candidum*, in order to obtain a mixture M containing AR mono-, di- and triglycerides, fatty acid esters other than AR, alcohol; ii) the step of separating said mixture M into at least two fractions, including a fraction A enriched with AR glycerides, and a fraction B enriched with fatty acid esters other than RA; iii) the step of converting said AR glycerides into AR esters consisting of a fraction C rich in AR esters and a fraction rich in alcohols.

8 Claims, 5 Drawing Sheets

(51) Int. Cl.
*C11C 3/00* (2006.01)
*C12P 13/00* (2006.01)

(56) References Cited

U.S. PATENT DOCUMENTS 5,633,151 A      5/1997   McNeill
5,713,965 A *    2/1998   Foglia et al. .................... 44/388
2010/0203600 A1 8/2010   Dubois

OTHER PUBLICATIONS

Gao, LeFei, e al., Primary study on producing biodiesel with castor oil by enzymatic catalysis, 2008, Anhui ogye Kexue, 36(16), pp. 6950 to 6952 (1 page abstract).*

DaSilva, et al., Optimizatin of Biodiesel production from castor oil, 2006, Applied Biochemixtry and Biotechnology, vol. 129-132, pp. 405-414.*

Chauvel, A., et al., Petrochemical processes, chapter 12, 1989, Editions Technip, Paris, (6 pages).*

FR 1023247, Alais & Froges & Camargue CIE, Purification of ricinoleic acid esters, 1953 English translation, 4 pages.*

Brown, J.B., et al., Studies on the chemistry of the fatty acids. V. The preparatin of methyl ricinoleat and ricinoleic acid by fractinal crystallizatin procedures, 1940, Journal of the American Chemical Society, vol. 62, No. 4, pp. 738-740.*

Vaysse, L., et al., Chain-length selectivity of various lipase during hydrolysis, esterification and alcoholysis in biphasic aqueous medium, 2002, Enzymer and Microbial Technology, No. 31, pp. 648-655.*

Foglia, T., et al., "Selectivity of Lipases: Isolation of Fatty Acids from Castor, Coriander, and Meadowfoam Oils", Eur J. Lipid Sci. Technol., (2000), pp. 612-617.

Naughton, F., "Production Chemistry and Commercial Applications of Various Chemicals from Castor Oil", Journal of the American Oil Chemists Society, (1974), pp. 65-71.

Breivik, H. et al.: "Preparation of highly Purified Concentrates of Eicosapentaenoic Acid and Docosahyxaenoic Acid", Journal of the American Oil Chemists Society, (1997), pp. 1425-1429.

Hayes, D., "Enzyme-Catalyzed Modification of Oilseed Materials to Produce Eco-friendly Products", Journal of the American Oil Chemists Society, (2004), pp. 1077-1103.

* cited by examiner

METHOD FOR PRODUCING RICINOLEIC ACID ESTER BY SELECTIVE ENZYMATIC TRANSESTERIFICATION

FIELD OF THE INVENTION

The present invention relates in general to the field of oliochemistry. More particularly, the invention relates to a method for preparing ricinoleic acid ester from a pure or mixed vegetable oil, in particular castor oil, said method comprising at least one step of enzymatic transesterification carried out in the presence of a light alcohol and by means of a typoselective lipase, and producing a fraction enriched with ricinoleic acid ester.

BACKGROUND OF THE INVENTION

Fatty acid esters are conventionally obtained by chemical transesterification of refined vegetable oil, in the presence of a catalyst, in particular an acid or basic catalyst. This route for producing fatty acid esters makes it possible to obtain said esters with good yields; however, it has many drawbacks, linked in particular to the need to eliminate the catalyst used, to the difficult recovery of the glycerol and to the high energy consumption. This collection of methods remains laborious, since it comprises many physicochemical conversion steps, which results in a high cost of the fatty acid esters thus produced. Furthermore, the acid or basic catalysts used are not selective with regard to the type of fatty acid, and transesterify all the fatty acid chains, producing a mixture of esters. However, it is very difficult to separate the various fatty acid esters, which have relatively close physical properties. In addition, this type of method does not make it possible to selectively extract the functionalized, in particular hydroxylated, fatty acid esters from the mixture of fatty acid esters obtained via the transesterification reaction. It so happens that it is desirable to have a fraction enriched with hydroxylated fatty acid esters, containing for example methyl ricinoleate (or methyl 12-hydroxy-cis-9-octa-decenoate), since such a fraction represents the starting point in the production of 11-aminoundecanoic acid, a constituent monomer of RILSAN 11, which is a polyamide with exceptional physical properties, developed by the applicant. During the production of 11-aminoundecanoic acid, methyl ricinoleate is subjected to gas-phase thermal cracking. To this effect, it must contain a minimum amount of glycerides, i.e. tri-, di- and monoglycerides, since these products are very difficult to vaporize, and often decompose before vaporization, which results in a reduction in the selectivity of the cracking. Similarly, the methyl ricinoleate must contain a minimum amount of ricinoleic acid, which is also difficult to vaporize.

In light of the aforementioned, the applicant set itself the objective of finding a method for transesterification of vegetable oils containing ricinoleic acid, which overcomes the abovementioned drawbacks of the known transesterification methods and makes it possible to obtain a fraction rich in ricinoleic acid ester.

Methods for esterification or hydrolysis of triglycerides contained in vegetable oils in the presence of lipases are well known. These enzymes have several advantages: they do not require a cofactor, are often commercially available and have a high activity and a high selectivity, even in nonaqueous systems. Esters of glycerol or triglycerides are their natural substrate. Some of these lipases exhibit positional specificity (or regioselectivity), which allows them to distinguish between the central position (sn-2) and the two external positions of glycerol (sn-1 and sn-3).

However, this specificity can be taken advantage of in the case of the ricinoleic acid (RA) present in castor oil only at the cost of a loss of yield, since the latter is composed predominantly of RA residues (from 85 to 90% by weight), the other fatty acid residues present being in particular those of oleic acid, linoleic acid, stearic acid, palmitic acid and linolenic acid. Ricinoleic acid preferably occupies the external positions, but can also be found in the internal position. Moreover, the literature does not describe any lipase that is specific for RA, in a transesterification reaction. Even the lipase extracted from the castor oil plant, which exhibits a preference for RA during the hydrolysis reaction, shows no typoselectivity with respect thereto.

Other lipases exhibit typoselectivity or specificity with respect to the nature of the fatty acid. It is thus known that the lipase extracted from *Geotrichum candidum*, a yeast-like fungus, exhibits strong specificity toward cis-9 monounsaturated fatty acids in esterification or hydrolysis reactions. Document DE 41 24 248 describes the use of extracellular lipases extracted from *Geotrichum candidum* for specifically cleaving oleic acid esters ($CH_3(CH_2)_7CH=CH(CH_2)_7COOH$). Document U.S. Pat. No. 5,633,151 describes the use of the same lipase for specifically cleaving erucic acid esters ($CH_3(CH_2)_7CH=CH(CH_2)_{11}COOH$).

The publication by Foglia T. A. et al., *Eur. J Lipid Sci. Technol.* 102 (2000): 612-617, describes the results of tests aimed at determining the selectivity of certain lipases toward fatty acids of plant origin. The results presented in table 1 show that the *Geotrichum candidum* lipase is discriminating toward ricinoleic acid (hereinafter denoted by RA), during the castor oil partial hydrolysis reaction carried out at 30° C. for 1 to 4 h with a commercial immobilized lipase. Moreover, the results represented in table 2 show that this enzyme is also discriminating toward RA during the reaction for esterification of a mixture of free fatty acids with 1-butanol. The esterification in the presence of *G. candidum* results, after 24 h of reaction, in a mixture consisting (amounts by mass) of 12% of fatty acid butyl esters and 88% of free fatty acids, the RA representing 94.5% of said free fatty acids. Said mixture therefore comprises approximately 83% of RA.

The particular behavior of an enzyme with respect to a substrate during a hydrolysis reaction does not make it possible to foresee its behavior toward the same substrate during a transesterification or esterification reaction. The specificity of a lipase varies from one type of reaction to another. The publication by Vaysse L. et al., *Enzyme Microb. Technol.* 31 (2002): 648-655 shows, through the results represented in tables 1 and 2, that the same lipase can have a different behavior toward the same fatty acid ester or the free fatty acid during the hydrolysis, transesterification and esterification reaction, respectively.

The applicant has carried out studies aimed at establishing the effect of the *Geotrichum candidum* lipase on the fatty acids present in castor oil, in particular on ricinoleic acid ($CH_3(CH_2)_5CH(OH)CH_2=CH(CH_2)_7COOH$) during the castor oil transesterification reaction. These studies have shown that, surprisingly, said lipase is discriminating toward RA in transesterification reactions in the presence of a light alcohol.

SUMMARY OF THE INVENTION

The object of the present invention is to provide a method of transesterification which allows the bioselective extraction of a ricinoleic acid ester, and therefore the production of a fraction enriched with this ester (containing more than 85% by weight of ester), from castor oil or any other oil containing RA residues.

To this effect, according to a first aspect, the invention relates to a method for producing ricinoleic acid ester from a vegetable oil containing ricinoleic acid, in particular castor oil, comprising the following steps:

i) a first transesterification reaction carried out in the presence of a light alcohol and of the lipase extracted from *Geotrichum candidum*, producing a mixture M comprising RA mono-, di- and triglycerides, esters of fatty acids other than RA, and alcohol;

ii) a step of separating said mixture M into at least two fractions, including a fraction A enriched with RA glycerides and a fraction B rich in esters of fatty acids other than RA;

iii) a step of converting said RA glycerides into RA esters forming a fraction C rich in RA esters and a fraction rich in alcohols.

Advantageously, said lipase selectively cleaves the ester bond involving fatty acids other than RA, in particular oleic acid and linoleic acid, and leaves virtually intact the acyl bonds involving an RA residue.

The implementation of the method according to the invention makes it possible to obtain a fraction C which is particularly rich in ricinoleic acid ester. Thus, according to a second aspect, the invention relates to a fraction enriched with RA ester containing at least 91% by weight, and preferably from 94 to 98% by weight, of ricinoleic acid methyl ester when the starting material is a pure castor oil. Such a fraction is very advantageously suitable for use as a starting material in the synthesis of intermediate chemical products such as 11-aminoundecanoic acid.

According to another embodiment, the implementation of the method according to the invention makes it possible to obtain a fraction C enriched with ricinoleic acid ester. Thus, according to a third aspect, when the starting material is an oil with a low ricinoleic acid content, as defined below, the method according to the invention makes it possible to obtain a fraction enriched with RA ester containing at least 75% by weight, and preferably from 82 to 91% by weight, of ricinoleic acid methyl ester. Such a fraction is particularly suitable for use as a starting material in the synthesis of intermediate chemical products such as 11-aminoundecanoic acid, since it then has a ricinoleic acid content equivalent to conventional castor oils.

Other characteristics and advantages will emerge from the detailed description of the method for producing ricinoleic acid ester according to the invention which follows and the appended FIGS. 1 to 10, representing:

DETAILED DESCRIPTION OF THE INVENTION

The present invention relates to a method for enzymatic transesterification of a vegetable oil containing ricinoleic acid, coupled to a method for chemical or enzymatic transesterification, for the purpose of producing a fraction rich in ricinoleic acid ester. Characteristically, the method uses an enzyme which exhibits an "anti"-selectivity (also referred to as discrimination) toward ricinoleic acid, i.e. which preferably transesterifies the chains other than ricinoleic acid. This effect is particularly demonstrated on the two main fatty acids other than ricinoleic acid of castor oil: oleic acid and linoleic acid.

The method for enzymatic transesterification of the invention is particularly suitable for an oil "with a low content" of ricinoleic acid, i.e. containing less than 82% by weight of ricinoleic acid. This situation is that of castor oils with a low ricinoleic acid content, or that of mixtures comprising castor oil and other vegetable oils originating from at least one other oleaginous, oleaginous/protein-producing or protein-producing plant, said mixtures containing at least 10% by weight of ricinoleic acid, or else that of oils originating from genetically modified plants producing ricinoleic acid, alone or as a mixture with oleaginous plants that have optionally been genetically modified and that contain at least 10% by weight of ricinoleic acid. With reference to the publications by Pilar Rijas-Barros in *Crop Science* 44 (2004): 76-80, and 45 (2005): 157-162, the expression "castor oil with a low ricinoleic acid content" is also understood to mean oils derived from mutants, such as OLE-1, described in these publications and which produce an oil containing approximately 10% of ricinoleic acid. With reference to the article by K. M. Hosamani in *Chemistry and Physics of Lipids*, 152 (2008) 9-12, the expression "oil with a low ricinoleic acid content" is also understood to mean the oil of *Hevea brasiliensis* and of *Jatropha gosypiifolia*, where ricinoleic acid has been found at a content of approximately 18%. With reference to another article by the same author, published in *Phytochemistry*, vol. 37, No. 6, pp. 1621-1624 in 1994, said expression is also understood to mean the oil of *Trichodesma zeylanicum*, which appears to contain 22% of ricinoleic acid. Mention may also be made of *Mammea africana* which contains 20% of ricinoleic acid in the seeds of its fruits, and also the oil of *Alternanthera triandra* Syn. *A. sessilis* seed, which contains approximately 22% thereof (K. M. Hosamani et al., *Industrial Crops and Products*, 2004, 19(2), 133-136). Consequently, the expression "vegetable oil containing ricinoleic acid" covers, in the context of the present invention, castor oil and also all these abovementioned oils and oil mixtures.

It has now been found that an extracellular lipase extracted from the *Geotrichum candidum* microorganism is selective with respect to fatty acids monounsaturated in the cis-9 position other than ricinoleic acid, during the reaction for transesterification of a vegetable oil containing ricinoleic acid, carried out in the presence of a light alcohol.

According to a first aspect, a subject of the invention is a method for producing ricinoleic acid ester from a vegetable oil containing ricinoleic acid, in particular castor oil, comprising the following steps:
i) a first enzymatic transesterification reaction carried out in the presence of a light alcohol and of the typoselective lipase extracted from a strain of *Geotrichum candidum*, producing a mixture M comprising RA mono-, di- and triglycerides, esters of fatty acids other than RA, and the alcohol;
ii) a step of separating said mixture M into at least two fractions, including a fraction A enriched with RA glycerides, and a fraction B rich in esters of fatty acids other than RA;
iii) a step of converting said RA glycerides contained in the fraction A into RA esters so as to form a fraction C rich in RA esters and a fraction rich in alcohols.

Advantageously, during step i), the duration of the transesterification reaction is at most 1 h, preferably at most 30 minutes, which corresponds to a content of at least 90% by weight of RA relative to the other fatty acids, in the partial glycerides fraction of the mixture M.

According to a first embodiment, step iii) of the transesterification method consists of a chemical transesterification reaction carried out on the phase comprising RA glycerides and alcohol, in the presence of a basic catalyst, such as sodium hydroxide, so as to obtain said fraction C rich in RA esters.

According to a second embodiment, step iii) consists of a second enzymatic transesterification reaction carried out in the presence of a light alcohol and of lipase for example chosen from *Candida antarctica* B (in particular in immobilized form N. 435 NOVO NORDISK), *Rhizomucor miehei* (in particular in immobilized form RM IM NOVOZYMES), *Thermomyces lanuginosa* (in particular in immobilized form TL IM NOVOZYMES), *Pseudomonas cepacia*, *Aspergillus niger*, *Rhizopus oryzae*, *Rhizopus arrhizus*, *Candida rugosa*, *Mucor javanicus*, porcine pancreatic lipase and any other lipase producing said fraction C rich in RA esters.

The light alcohol used is a lower aliphatic alcohol such as methanol, ethanol, isopropanol and n-propanol, and is preferably methanol.

The substrate/alcohol ratio in step i) ranges from 1:4.5 to 1:0.75, the alcohol being added in one or more additions.

Given the composition of castor oil (see example 1), the most predominant esters of fatty acids other than RA are oleic acid esters and linoleic acid esters. Step ii) of separating the mixture of ricinoleic acid glycerides/methyl esters of oleic/linoleic acids comprises at least one operation chosen from: distillation, centrifugation, decanting, liquid-liquid extraction by means of apolar organic solvents such as, for example, hexane or petroleum ether, and chromatographic separation by selective adsorption.

*Geotrichum candidum* is an endomycete of the family Dipodascaceae, which has a morphology close to filamentous fungi. It is widespread in the wild and is found in many foods, including dairy products. It is also a saprophyte of the digestive tract in humans and animals.

The expression "lipase extracted from *Geotrichum candidum*" is intended to mean herein both the crude mixture of extracellular lipases extracted from this yeast, according to the protocol described for example in document DE 41 24 248, and an enzyme obtained by heterologous expression of a *Geotrichum candidum* gene encoding one of these lipases.

With the objective of providing a good yield for the purpose of use on the industrial scale, this enzyme is preferably used in the context of the invention in an immobilized form.

The conditions for using the lipase of *Geotrichum candidum* during the transesterification phase are the following:
temperature included in the range of from 20 to 40° C., preferably approximately 30° C.;
lipase/substrate ratio greater than or equal to 0.5%;
sufficient agitation for good homogenization of the reaction medium of batch type, or a sufficient flow rate for an optimum contact time (catalytic bed);
atmospheric pressure or higher depending on the method implemented.

The method is carried out at low temperature and a pressure close to atmospheric pressure. The residence times are also limited since the intention is not to convert all the fatty chains, but only the impurities that are present (fatty acids other than ricinoleic acid).

In one embodiment variant, the fraction C containing the ricinoleic acid ester resulting from the method according to the invention can advantageously be directly used in the synthesis of 11-aminoundecanoic acid. When the ricinoleic acid ester is not sufficiently pure, an additional purification step may be necessary, before subjecting it to the pyrolysis reaction.

The 11-aminoundecanoic acid thus obtained is intended mainly for the synthesis by condensation of polyamide 11 or Rilsan® 11, according to the following series of reactions:
pyrolysis or cracking of the ricinoleic acid ester, in particular methyl ester, producing heptanal and methyl undecylenate;
hydrolysis of the methyl undecylenate, producing undecylenic acid;
hydrobromination of the undecylenic acid, producing 11-bromoundecanoic acid, and
amination of the 11-bromoundecanoic acid, producing 11-aminoundecanoic acid.

According to one embodiment variant, the fraction B enriched with esters of fatty acids other than RA is subjected to a succession of chemical and/or physical reactions, producing biodiesel. The fatty acid esters may in this case be subjected to separation reactions by various additional separative techniques, for example by distillation, including molecular distillation, by liquid-liquid extraction (counter-current chromatography in a methanol/hexane medium) or by simulated moving bed chromatographic separation.

The invention will be understood more clearly on reading the following nonlimiting exemplary embodiments.

1. Fatty Acid Composition of Castor Oil

A sample of castor oil originating from India was analyzed with regard to its fatty acid composition. For this determination, the oil is converted into methyl esters according to a procedure comprising two successive steps, a basic methanolysis followed by an acidic esterification. In the first step, the glycerides (mono-, di- and triglycerides) are converted into methyl esters through the action of sodium methoxide, and the free fatty acids, which may be present, are converted into soaps. The addition of a methanolic solution of ethanoyl chloride results, during the second step, in the conversion of these soaps into methyl esters. The methyl esters thus obtained are then analyzed by gas chromatography (Agilent 6890 series GC, equipped with a flame ionization detector—FID). The separations are carried out on a Supelcowax 10 column (Agilent Technologies, 30 m×0.32 mm×0.25 µm; vector gas: helium at 1 ml/min; initial oven temperature 150° C., temperature program of 5° C./minute up to 225° C. and hold for 7 min at this temperature).

The main fatty acids identified by this technique are:
ricinoleic acid 86.0% by weight;
linoleic acid 5.3% by weight;
oleic acid 4.1% by weight;
stearic acid 1.5% by weight;
palmitic acid 1.3% by weight.

2. Production of the Typoselective Lipase of *Geotrichum candidum*

The operating protocol described in document DE 41 24 248 was used to obtain the crude extract of extracellular lipases derived from this yeast. Moreover, the lipase was also obtained by fermentation of the yeast *Pichia pastoris* by means of a recombinant technology. Thus, at the end of 30 h of fermentation, the fermentation supernatant containing the extracellular lipase is collected. At this stage, the supernatant is characterized by a protein concentration of 2.46 mg/ml and a specific hydrolytic activity measured on ethyl oleate (30° C.) of 90 U/ml (with U=1 µmol of ethyl ester hydrolyzed per min at 30° C., pH 6.5). The supernatant is then subjected to a series of filtrations aimed at clarifying it and concentrating it without affecting the specific activity of the lipase that it contains: i) membrane microfiltrations (cutoff thresholds 5 µm then 0.45 µm), membrane ultrafiltration aimed at concentrating the supernatant 14-fold, then diafiltration against a 50 mM sodium phosphate buffer solution, pH 6.5. The concentrate obtained has a protein content of 18 mg/ml and a specific activity of 522 U/ml on ethyl oleate and 900 U/ml on olive oil (30° C.)

Immobilization of the Lipase

The mixture of lipases extracted from *Geotrichum candidum* (or the concentrate obtained after fermentation according to the protocol described above) was immobilized on a support chosen from:
microporous polypropylene, for example of the ACCUREL MP 1000 type, manufactured by Accurel Systems, Membrana GmbH, Obernburg, Germany;
DEAE cellulose;
Celite (diatomite).

By way of example, the immobilization of the typoselective lipase of *Geotrichum candidum* on Accurel® MP 1000 comprises, in a first step, a physical adsorption, followed in a second step by a crosslinking in the presence of glutaraldehyde.

3. Activity and Specificity of the Free Typoselective Lipase of *Geotrichum candidum* on a Model Substrate, in a Transesterification Reaction in the Presence of Methanol The activity of the free typoselective lipase of *Geotrichum candidum* in a transesterification reaction in the presence of methanol was compared with that of commercial enzymes (*C. antarctica* B, N 435, NOVO NORDISK; *R. oryzae*, FAP 15, Amano; *R. Mieihei*, LIPOZYME RL-IM, NOVOZYMES; TL-IM, LIP, NOVOZYMES). An equimolar mixture of ethyl esters of oleic, linoleic and ricinoleic acids (ethyl oleate, ethyl linoleate, ethyl ricinoleate) is brought into contact with the enzyme (lipase/substrate weight ratio: 5%). The methanol is added at a methanol/substrate molar ratio of 1.5:1, and then the mixture is incubated for 24 h at 30° C. The methyl esters formed are quantified by gas chromatography according to the method detailed in example 1. The results obtained are given in the appended FIG. 1, which illustrates the degree of conversion of ethyl esters into methyl esters in a transesterification reaction in the presence of methanol, obtained with the free typoselective lipase of *Geotrichum candidum* and various commercial lipases (24 h, 30° C., 3 replicates, lipase/substrate ratio=1.5% w/w, methanol/substrate molar ratio=1.5:1).

Figure 1:
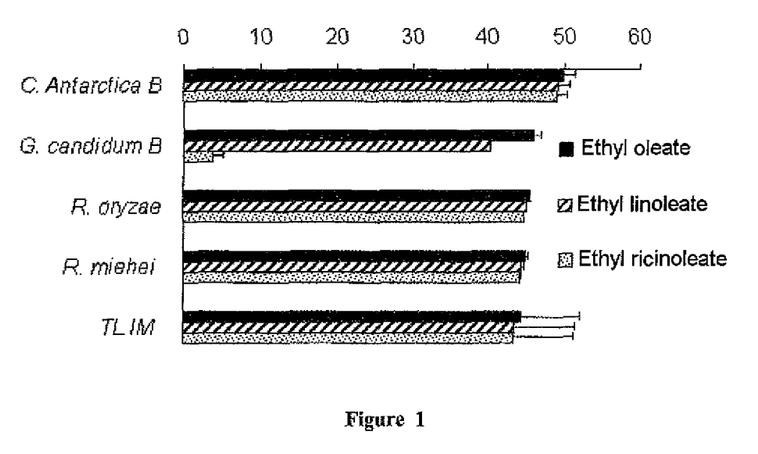
FIG. 1 illustrates the degree of conversion of ethyl esters to methyl esters in the transesterification reaction in the presence of methanol, obtained with a typoselective lipase of *Geotrichum candidum* in free form and various commercial lipases.

Regardless of the enzyme, conversion rates of between 40% and 50% are obtained for the ethyl oleate and the ethyl linoleate. With regard to the ethyl ricinoleate, only the typoselective lipase of *Geotrichum candidum* produces a conversion of less than 40%, with a value of between 2% and 5%. These results indicate a very strong selectivity of action of the typoselective lipase of *G. candidum* toward the oleoyl and linolenoyl groups and, consequently, a discrimination toward the ricinoleoyl groups.

4. Activity and Specificity of the Free Typoselective Lipase of *Geotrichum candidum* on Castor Oil, in a Transesterification Reaction in the Presence of Methanol The methanolysis reactions are carried out at 30° C., at atmospheric pressure, in the presence of molecular sieves (3 Å, Perlform, Ø 2 mm) with an amount of 10% w/w of the substrate (castor oil). The *G. candidum* typoselective lipase concentrate protein/substrate ratio is adjusted to 1.5% w/w and a methanol/castor oil triglycerides molar ratio of 4.5:1 was established in three successive additions at 0, 2 and 4 hours of reaction. The whole of the reaction medium is homogenized by vortex (10 s). At various times, aliquots are removed from the reaction medium, and diluted in acetone/acetonitrile (1:1 v/v) before being analyzed by the chromatographic techniques mentioned below.

It was possible to characterize the transesterification reaction kinetics by thin layer chromatography (TLC) and high performance liquid chromatography (HPLC). More specifically, TLC made it possible to visualize the classes of lipid entities formed, while some of these entities could be quantified by HPLC following the establishment of calibration curves.

The TLC separations were carried out by depositing, onto glass plates precoated with silica (100×200 mm, Si G 60, Merck), samples dissolved at 10 mg/ml in acetone/acetonitrile (50/50 v/v). The deposits (10 µl) were carried out with an automatic depositing device (Linomat IV, Camag). After elution with a mobile phase consisting of hexane/diethyl ether/acetic acid (40:60:1 v/v), the entities present were revealed by spraying with a saturated solution of copper sulfate and phosphoric acid (50:50 v/v) and incubating (10 minutes, 180° C.).

The retention factors given in table I below were determined by comparison with standard compounds.

TABLE I

| Lipid classes | Retention factor* |
|---|---|
| Monoricinolein | 0.02 |
| Nonhydroxylated monoglycerides | 0.07 |
| Diricinolein | 0.13 |
| Monohydroxylated diglycerides (1, 2) | 0.17 |
| Monohydroxylated diglycerides (1, 3) | 0.22 |
| Triricinolein (RRR) | 0.36 |
| Ricinoleic acid (RA) | 0.42 |
| Dihydroxylated triglycerides | 0.47 |
| Methyl ricinoleate | 0.58 |
| Nonhydroxylated fatty acids | 0.65 |
| Monohydroxylated triglycerides | 0.69 |
| Other esters | 0.95 |

*Retention factor = entity migration distance/solvent front migration distance

The separation of the products by HPLC was carried out using an automated system (Thermo-Finningan, Courtaboeuf, France) based on a pump (P1000 XR), a sample changer (AS 1000) and a light scattering detector (Alltech 500 ELSD). Two Interchim C18 columns (5 µm; 4.6×250 mm, Modulo Cart QS, Lichrosphere 500 DS 2) mounted in series were used for the separation. The samples (1 mg/ml) were eluted according to a gradient of a mixture of acetone/acetonitrile/formic acid (70:30:1, v/v; X) and of chloroform (Y). The elution was carried out at a flow rate of 1 ml/min according to the following linear gradient: 0 min 100% X, 30 min 90% X, 50 min 90% X, return to the initial conditions over the course of 5 min and holding of these conditions for a further 15 min.

The retention times for the main entities analyzed by HPLC according to the protocol described above are given in table 2 hereinafter.

The products obtained during the transesterification in the presence of methanol are essentially ricinoleic acid (RA), linoleic acid (LA), oleic acid (OA) and the corresponding methyl esters, methyl ricinoleate (MeRA), methyl linoleate (MeLA) and methyl oleate (MeOA).

TABLE II

| Entitles analyzed | Retention time (min) |
|---|---|
| Ricinoleic acid | 7.2 |
| Methyl ricinoleate | 8.1 |
| Monoricinolein | 9.3 |
| Linoleic acid | 9.5 |
| Diricinolein | 11.5 |
| Methyl linoleate | 11.8 |
| Oleic acid | 12.3 |
| Methyl oleate | 14.6 |
| Triricinolein | 19.8 |
| Trilinolein | 22.6 |

Figure 2:
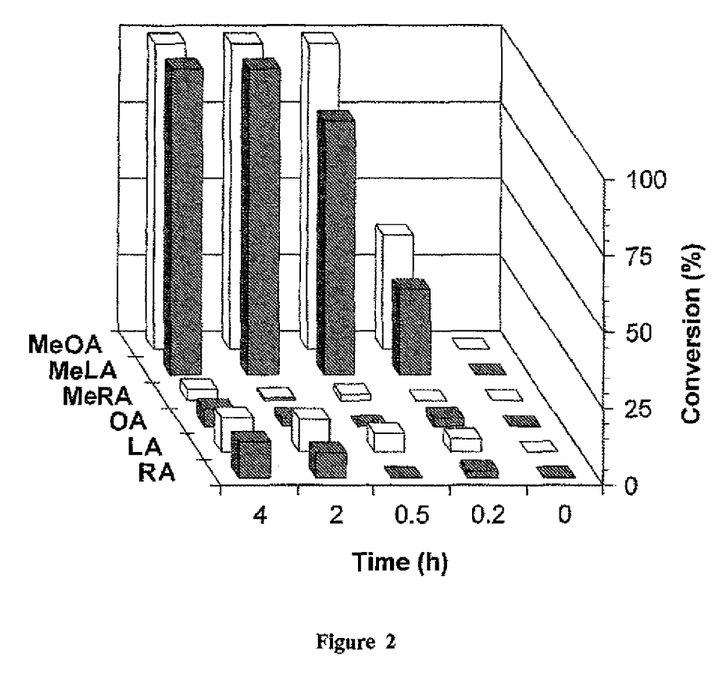
FIG. 2 shows the kinetics for conversion of the ricinoleoyl, linoleoyl and oleoyl groups initially in the form of glycerides in castor oil into methyl esters or corresponding fatty acids during the transesterification reaction in the presence of methanol, catalyzed by the typoselective lipase of *G. candidum*.

The kinetics for conversion of the ricinoleoyl, linoleoyl and oleoyl groups, initially present in the form of glycerides in castor oil, into methyl esters or corresponding fatty acids during the transesterification reaction in the presence of methanol, catalyzed by the typoselective lipase of *G. candidum* (30° C., 3 replicates, lipase extract proteins/substrate ratio=1.5% w/w, methanol/triglycerides molar ratio=4.5:1 in 3 fractionated additions at t=0, 2 and 4 h), are illustrated in FIG. 2.

Figure 3:
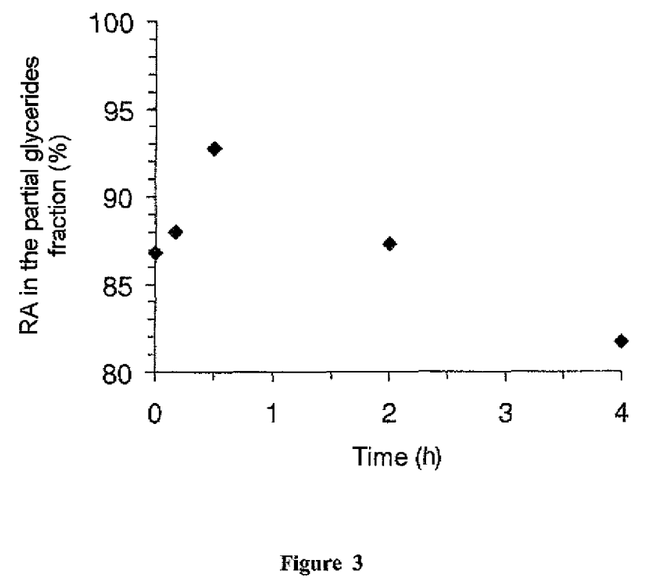
FIG. 3 illustrates the change in the RA concentration in the partial glycerides fraction during the transesterification of castor oil in the presence of methanol, catalyzed by the typoselective lipase of *G. candidum*.

The conversion of the ricinoleoyl, linoleoyl and oleoyl groups (initially esterified in the castor oil) into fatty acids and methyl esters results in the appearance of a partial glycerides fraction of which the RA content is at its maximum between 0.5 h and 2 h of reaction. The appended FIG. 3 illustrates the change in the RA concentration in the partial glycerides fraction during the transesterification of the castor oil in the presence of methanol, catalyzed by the typoselective lipase of *G. candidum* (30° C., 3 replicates, lipase extract proteins/substrate ratio=1.5% w/w, methanol/triglycerides molar ratio=4.5:1 in 3 fractionated additions at t=0, 2 and 4 h).

5. Activity and Specificity of the Free Typoselective Lipase of *Geotrichum candidum* on Castor Oil in a Mixture, in a Transesterification Reaction in the Presence of Methanol In all the examples below, the methanolysis reactions were carried out under conditions similar to those stated in example 3.

5.1 Castor Oil/Trilinolein 50/50 w/w

Figure 4:
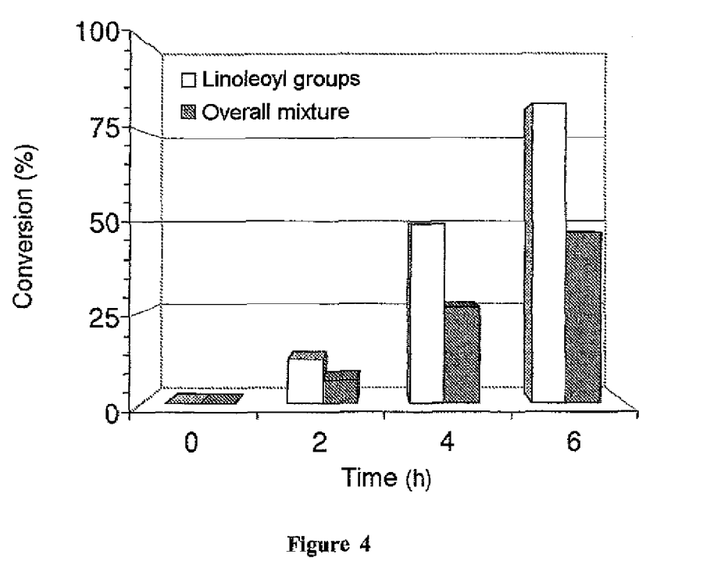
FIG. 4 shows a comparison of the kinetics for conversion of the linoleoyl groups and of the acyl groups into methyl esters during a reaction for transesterification, in the presence of methanol, of a 50:50 w/w (by weight) castor oil/trilinolein mixture, catalyzed by the typoselective lipase of *G. candidum*.

The appended FIG. 4 shows a comparison of the kinetics for conversion of the linoleoyl groups and of the acyl groups into methyl esters during a transesterification reaction, in the presence of methanol, carried out on a 50:50 w/w castor oil/trilinolein mixture, catalyzed by the typoselective lipase of *G. candidum* (30° C., 3 replicates, lipase extract proteins/substrate ratio=1.5% w/w, a methanol/triglycerides molar ratio of 4.5:1 in 3 fractionated additions at t equal to 0, 2 and 4 h). A degree of conversion of 80% of the linoleoyl groups initially esterified in the oil mixture is reached in 6 hours of reaction.

The ratio of the ricinoleoyl groups to all the ricinoleoyl and linoleoyl groups in the reaction products is characteristic of the discrimination of the lipase toward the ricinoleoyl group and, conversely, of its selectivity toward the linoleoyl group.

Figure 5:
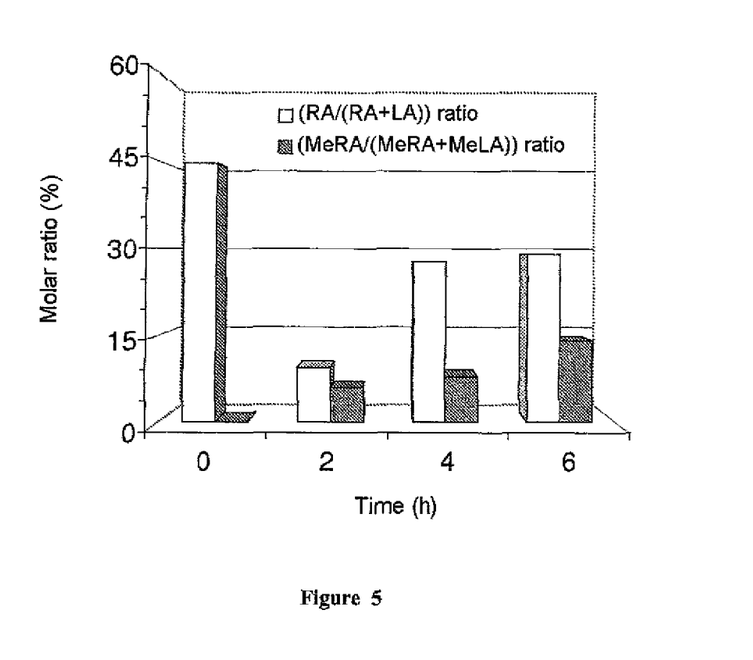
FIG. 5 illustrates the change in the [RA/(RA+LA)] and [MeRA/(MeRA+MeLA)] ratios representative of the discrimination of a typoselective lipase of *G. candidum* for the ricinoleoyl groups and of its selectivity for the linoleoyl groups during a reaction for transesterification, in the presence of methanol, of a 50:50 w/w castor oil/trilinolein mixture, catalyzed by the typoselective lipase of *G. candidum*.

In parallel to this methanolysis reaction, the water molecules provided by the lipase concentrate lead to the formation of free fatty acids (RA, LA) via a hydrolysis reaction. This discrimination is greater in the methanolysis reaction than in the hydrolysis reaction, as represented in the appended FIG. 5. This figure illustrates the change in the [RA/(RA+LA)] and [MeRA/(MeRA+MeLA)] ratios representative of the discrimination of the typoselective lipase of *G. candidum* toward the ricinoleoyl groups and of its selectivity toward the linoleoyl groups during a transesterification reaction, in the presence of methanol, carried out on a 50:50 w/w castor oil/trilinolein mixture, catalyzed by the typoselective lipase of *G. candidum* (30° C., 3 replicates, a lipase extract proteins/substrate ratio of 1.5% w/w, a methanol/triglycerides molar ratio of 4.5:1 in 3 fractionated additions at t equal to 0, 2 and 4 h).

Figure 6:
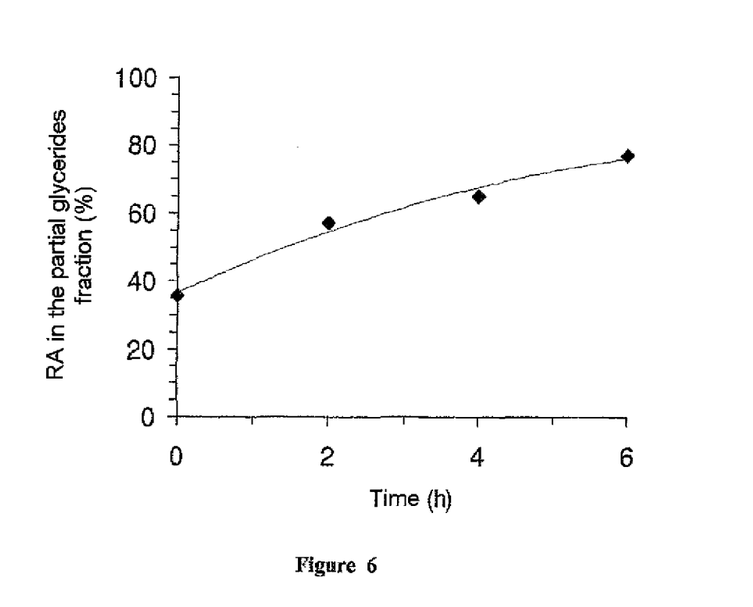
FIG. 6 presents the change in the RA concentration in the partial glycerides fraction during the transesterification, in the presence of methanol, of a 50:50 w/w castor oil/trilinolein mixture, catalyzed by the typoselective lipase of *G. candidum*.

Finally, this discrimination leads to the enrichment of an initial RA concentration of 35% (RA in the form of glycerides in the starting oil mixture) to more than 77% in the partial glycerides fraction of the reaction medium after 6 h of reaction, as represented in the appended FIG. 6, which illustrates the change in the RA concentration in the partial glycerides fraction during the transesterification, in the presence of methanol, of a 50:50 w/w castor oil/trilinolein mixture, catalyzed by the typoselective lipase of *G. candidum* (30° C., 3 replicates, a lipase extract proteins/substrate ratio of 1.5% w/w, a methanol/triglycerides molar ratio of 4.5:1 in 3 fractionated additions at t equal to 0, 2 and 4 h).

5.2 Castor Oil/Trilinolein 10/90 w/w

Figure 7:
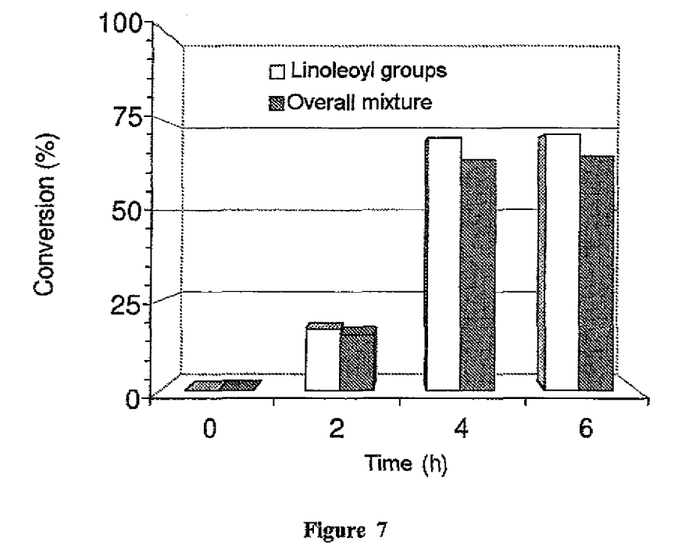
FIG. 7 illustrates the comparison of the kinetics for conversion of the linoleoyl groups and of the acyl groups into methyl esters during a reaction for transesterification, in the presence of methanol, of a 90:10 w/w castor oil/trilinolein mixture, catalyzed by the typoselective lipase of *G. candidum*.

The kinetics for conversion of the linoleoyl groups and of the acyl groups into methyl esters during a transesterification reaction, in the presence of methanol, carried out on a 90:10 w/w castor oil/trilinolein mixture, catalyzed by the typoselective lipase of *G. candidum* (30° C., 3 replicates, a lipase extract proteins/substrate ratio of 1.5% w/w, a methanol/triglycerides molar ratio of 4.5:1 in 3 fractionated additions at t equal to 0, 2 and 4 h), were compared and the results obtained are shown in the appended FIG. 7.

Figure 8:
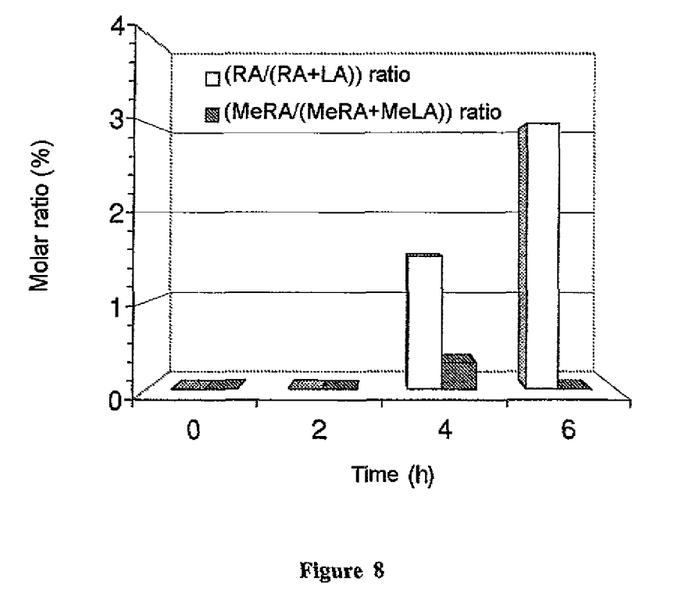
FIG. 8 illustrates the change in the [RA/(RA+LA)] and [MeRA/(MeRA+MeLA)] ratios representative of the discrimination of the typoselective lipase of *G. candidum* toward the ricinoleoyl groups and of its selectivity toward the linoleoyl groups during a reaction for transesterification, in the presence of methanol, of a 90:10 w/w castor oil/trilinolein mixture.

FIG. 8 shows the change in the [RA/(RA+LA)] and [MeRA/(MeRA+MeLA)] ratios representative of the discrimination of the typoselective lipase of *G. candidum* toward the ricinoleoyl groups and of its selectivity toward the linoleoyl groups during a transesterification reaction, in the presence of methanol, carried out on a 90:10 w/w castor oil/trilinolein mixture (30° C., 3 replicates, a lipase extract proteins/substrate ratio of 1.5% w/w, a methanol/triglycerides molar ratio of 4.5:1 in 3 fractionated additions at t equal to 0, 2 and 4 h).

Figure 9:
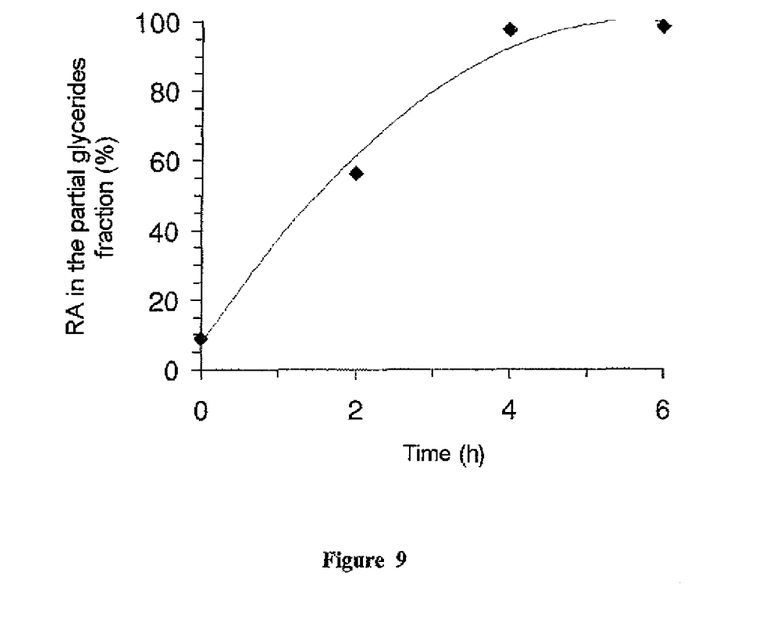
FIG. 9 shows the change in the RA concentration in the partial glycerides fraction during the transesterification, in the presence of methanol, of a 90:10 w/w castor oil/trilinolein mixture, catalyzed by the typoselective lipase of *G. candidum*.

FIG. 9 shows the change in the RA concentration in the partial glycerides fraction during the transesterification, in the presence of methanol, of a 90:10 w/w castor oil/trilinolein mixture, catalyzed by the typoselective lipase of *G. candidum* (30° C., 3 replicates, a lipase extract proteins/substrate ratio of 1.5% w/w, a methanol/triglycerides molar ratio of 4.5:1 in 3 fractionated additions at t equal to 0, 2 and 4 h).

5.3 Castor Oil/Linseed Oil 50/50 w/w

The linseed oil used as a mixture with the castor oil is composed of glycerides comprising predominantly linolenoyl (45%), linoleoyl (25%) and oleoyl (19%) groups. Under reaction conditions similar to those stated in example 3, an overall degree of conversion of these acyl groups into methyl esters of 17% is reached after two hours. The level of methyl ricinoleate (MeRA) in the methyl esters fraction is then 6%. These results indicate a selectivity of the typoselective lipase of *G. candidum* toward the linolenoyl groups which is similar to the selectivity toward the linoleoyl groups.

5.4 Castor Oil/Linseed Oil 10/90 w/w

Under reaction conditions similar to those stated in example 3, an overall degree of conversion of these acyl groups into methyl esters of 12% is reached after two hours. The level of methyl ricinoleate (MeRA) in the methyl esters fraction is then 2%.

Figure 10:
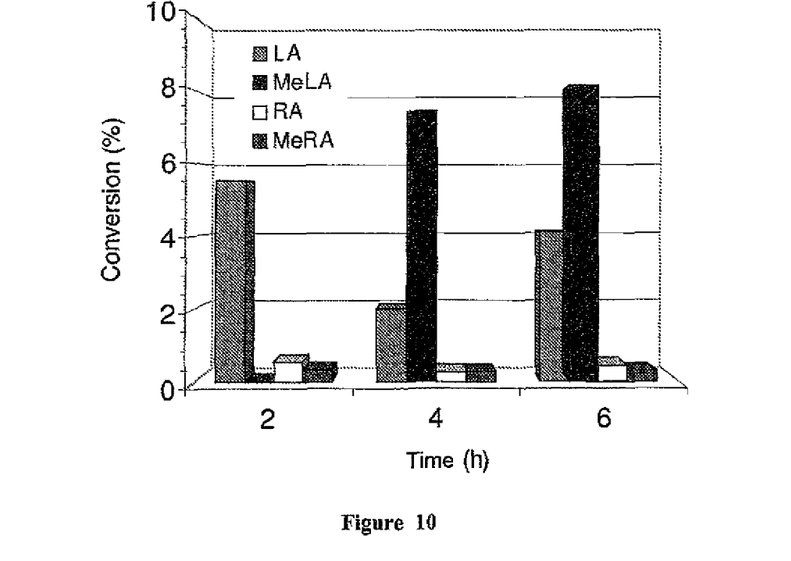
FIG. 10 presents the kinetics for conversion of the ricinoleoyl and linoleoyl groups initially in the form of glycerides, into methyl esters or corresponding fatty acids, during the reaction for transesterification of a 50:50 w/w castor oil/trilinolein mixture, in the presence of methanol, catalyzed by the immobilized typoselective lipase of *G. candidum*.

6. Activity and Specificity of the Immobilized Typoselective Lipase of *Geotrichum candidum* on Castor Oil in a Mixture, in a Transesterification Reaction in the Presence of Methanol The typoselective lipase of *Geotrichum candidum*, immobilized on an ACCUREL MP 1000 support, was tested in a transesterification reaction in the presence of methanol on a 50:50 w/w castor oil/trilinolein mixture (30° C., 3 replicates, an enzyme/substrate ratio of 1.5% w/w, a methanol/triglycerides molar ratio of 1.5:1). FIG. 10 illustrates the kinetics for conversion of the ricinoleoyl and linoleoyl groups, initially in the form of glycerides, into methyl esters or corresponding fatty acids, during the transesterification reaction carried out on a 50:50 w/w castor oil/trilinolein mixture, in the presence of methanol, catalyzed by the immobilized typoselective lipase of *G. candidum* (30° C., 3 replicates, an enzyme/substrate ratio of 1.5% w/w, a methanol/triglycerides molar ratio of 1.5:1). These results show that the immobilized lipase retains its very strong selectivity toward the linoleoyl groups, despite a significant decrease in its activity. The hydration of the immobilized enzyme ($a_w$=0.96) results in hydrolysis reactions and the appearance of free fatty acids together with the methyl esters.

The invention claimed is:

1. A method for producing ricinoleic acid (RA) ester from castor oil comprising the following steps:

i) transesterifying in a enzymatic transesterification reaction, carried out in the presence of a lower aliphatic alcohol selected from the group consisting of methanol, ethanol, isopropanol, and n-propanol and of the lipase extracted from *Geotrichum candidum*, producing a mixture M comprising RA mono-, di- and triglycerides, esters of fatty acids other than RA, and alcohol, wherein the lipase extracted from *Geotrichum candidum* is immobilized on a support which is inorganic or organic, of cellulosic nature, or a synthetic polymer, wherein the reaction temperature during the use of said lipase extracted from *Geotrichum candidum* is in the range of from 20 to 40° C., and wherein the reaction time is at most 1 hour, the lipase/substrate ratio is at least 0.5% w/w, and the substrate/alcohol ratio ranges from 1:4.5 to 1:0.75 the alcohol being added in one or more additions;

ii) separating said mixture M into at least two fractions, including a fraction A enriched with RA glycerides, and a fraction B rich in esters of fatty acids other than RA; and iii) converting said RA glycerides contained in the fraction A into RA esters so as to form a fraction C rich in RA esters and a fraction rich in alcohols.

2. The method as claimed in claim 1, in which step iii) consists of a chemical transesterification reaction carried out on the phase comprising RA glycerides and alcohol, in the presence of a basic catalyst, so as to obtain said fraction C rich in RA esters.

3. The method as claimed in claim 1, in which step iii) consists of a second enzymatic transesterification reaction, producing said fraction C rich in RA esters and carried out in the presence of a lower aliphatic alcohol and of a lipase selected from the group consisting of:

lipases extracted from: *Candida antarctica* B, *Rhizomucor miehei*, *Thermomyces lanuginosa*, and *Rhizopus oryzae*.

4. The method as claimed in claim 1, in which step ii) of separating the mixture M comprises at least one operation chosen from: distillation, centrifugation, decanting, liquid-liquid extraction by means of apolar organic solvents, and chromatographic separation by selective adsorption.

5. The method as claimed in claim 1, in which said fraction C enriched with RA esters is subjected to a succession of chemical reactions, producing 11-aminoundecanoic acid.

6. The method as claimed in claim 1, in which said fraction B enriched with esters of fatty acids other than RA is subjected to a succession of chemical and/or physical reactions, producing biodiesel.

7. The method of claim 1, wherein step iii) consists of a second enzymatic transesterification reaction, producing said fraction C rich in RA esters and carried out in the presence of a lower aliphatic alcohol and of a lipase extracted from *Geotrichum candidum*.

8. The method of claim 7, wherein said lipase extracted from *Geotrichum candidum*, used in step iii), is immobilized on a support which is inorganic or organic, of cellulosic nature, or a synthetic polymer.

* * * * *